United States Patent [19]

Crawford

[11] Patent Number: 4,652,658

[45] Date of Patent: Mar. 24, 1987

[54] PROCESS FOR MAKING 2-OXINDOLE-1-CARBOXAMIDES AND INTERMEDIATES THEREFOR

[75] Inventor: Thomas C. Crawford, Ledyard, Conn.

[73] Assignee: Pfizer Inc., New York, N.Y.

[21] Appl. No.: 888,297

[22] Filed: Jul. 22, 1986

Related U.S. Application Data

[60] Division of Ser. No. 754,318, Jul. 12, 1985, which is a division of Ser. No. 684,889, Dec. 21, 1984, abandoned, which is a continuation-in-part of Ser. No. 590,667, Mar. 19, 1984, abandoned.

[51] Int. Cl.[4] .................... C07D 209/34; C07D 405/02
[52] U.S. Cl. .................................. 548/468; 548/431; 548/486
[58] Field of Search ....................... 548/431, 486, 468

[56] References Cited

U.S. PATENT DOCUMENTS 3,923,996 12/1975 Hardtmann .................... 548/431 X

FOREIGN PATENT DOCUMENTS 0175551 3/1986 European Pat. Off. ............ 548/468

OTHER PUBLICATIONS

Graf, *Angew. Chem. Internat. Edit.*, 7, (1968), pp. 172–182.
Rasmussen et al., *Chem. Rev.*, 76, (1976), pp. 389–408.
Szabo, *Aldrichimica Acta*, 10, (1977), pp. 23–29.

*Primary Examiner*—Joseph Paul Brust
*Attorney, Agent, or Firm*—Charles J. Knuth; Peter C. Richardson; J. Trevor Lumb

[57] ABSTRACT

Preparation of 2-oxindole-1-carboxamides by reaction of 2-oxindoles with chlorosulfonyl isocyanate to produce novel N-chlorosulfonyl-2-oxindole-1-carboxamides which are then hydrolyzed to 2-oxindole-1-carboxamides useful as intermediates for analgesic and antiinflammatory agents.

4 Claims, No Drawings

PROCESS FOR MAKING 2-OXINDOLE-1-CARBOXAMIDES AND INTERMEDIATES THEREFOR

CROSS-REFERENCE TO RELATED APPLICATIONS

This application is a division of application Ser. No. 754,318, filed July 12, 1985, which is a division of application Ser. No. 684,889, filed Dec. 21, 1984, now abandoned, which is a continuation-in-part of application Ser. No. 590,667, filed Mar. 19, 1984, now abandoned.

BACKGROUND OF THE INVENTION

This invention relates to a process for making 2-oxindole-1-carboxamides which comprises reacting a 2-oxindole with chlorosulfonyl isocyanate to produce a novel N-chlorosulfonyl-2-oxindole-1-carboxamide which is then hydrolyzed to a 2-oxindole-1-carboxamide. Said 2-oxindole-1-carboxamides are useful as intermediates for analgesic and antiinflammatory agents.

The reactions of chlorosulfonyl isocyanate with various nucleophiles, including amines to produce N-chlorosulfonylamido ($ClSO_2NHCO$) derivatives thereof, and subsequent hydrolysis of said derivatives to afford amides is described by Graf., Angew. Chem. Internat Edit, 7, 175 (1968); Rasmussen et al., Chem. Rev. 389–390 (1976); and Szabo, Aldrichimica Acta 10, 23 (1977).

The preparation of 2-oxindole-1-carboxamides by cyclization of the appropriate (2-ureidophenyl)acetic acid by means of, for example, trifluoroacetic anhydride/trifluoroacetic acetic acid is described in U.S. patent application Ser. No. 684,634, filed Dec. 21, 1984, now U.S. Pat. No. 4,556,672, of Saul B. Kadin, entitled 3-Substituted 2-Oxindole-1-carboxamides as Analgesic and Anti-inflammatory Agents.

The process of this invention represents an improved process for making 2-oxindole-1-carboxamides of formula III in good yield and purity from starting materials which are readily available.

Summary of the Invention

This invention provides a convenient process for making 2-oxindole-1-carboxamides by reaction of a 2-oxindole with chlorosulfonyl isocyanate to produce a novel intermediate N-chlorosulfonyl-2-oxindole-1-carboxamide which is then hydrolyzed to a 2-oxindole-1-carboxamide. The process, the intermediate and the final products are presented below:

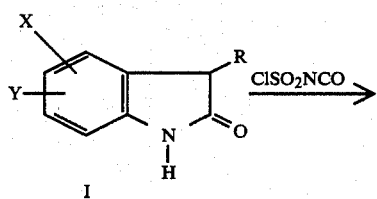

wherein R is hydrogen or —CO—$R^1$, wherein $R^1$ is as defined below, and

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6-or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of $Z^1$, $Z^2$, $Z^3$, and $Z^4$ and $Z^5$ wherein W is oxygen or sulfur.

Compounds of formula III wherein R is hydrogen are valuable intermediates for preparation of analgesic and antiinflammatory compounds of formula IV:

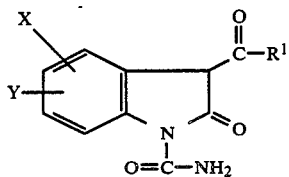

wherein X and Y are as defined above; and $R^1$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl, naphthyl, bicyclo[2.2.1]heptan-2-yl, bicyclo[2.2.1]hept-5-en-2-yl and $-CH_2)_n-Q-R°$;

wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl; n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]-thiophene; and R° is hydrogen or alkyl having 1 to 3 carbons.

Favored compounds of formula IV are those wherein: (i) one of X and Y is hydrogen and the other is 5- or 6- chloro, fluoro or trifluoromethyl; or (ii) X is 5-chloro or 5-fluoro and Y is 6-chloro or 6-fluoro. Said compounds exhibit a higher level of analgesic and antiinflammatory activity than do other of said formula IV compounds.

DETAILED DESCRIPTION OF THE INVENTION

Thus, the process of this invention is useful for preparing analgesic and antiinflammatory compounds of the formula IV, wherein X, Y and $R^1$ are as defined previously. These compounds are derivatives of 2oxindole, the bicyclic amide of the formula

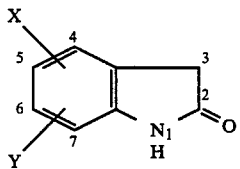

More particularly, these analgesic and antiinflammatory agents have a carboxamido substituent, $-C(=O)-NH_2$, at the 1-position and an acyl substituent, $-C(=O)-R^1$, at the 3-position of 2-oxindole, and the benzo ring can be further substituted by X and Y groups. X and Y can be certain monovalent substituents as defined previously, or X and Y when on adjacent carbon atoms on the benzo ring can represent a methylenedioxy group, $-OCH_2O-$, or an ethylenedioxy group, $-OCH_2CH_2O-$. Yet further, X and Y, when they are attached to adjacent carbon atoms of the benzo ring of the 2-oxindole, can form a divalent unit, Z, such that when Z is taken with the carbon atoms to which it is attached it forms a fused carbocyclic or heterocyclic ring. Certain divalent groups for Z (i.e. $Z^1-Z^5$) have been listed earlier. Thus, when Z is $Z^1$, X and Y when taken with the carbons to which they are attached represent a fused cyclopentene ring; and when Z is $Z^5$, X and Y when taken with the carbons to which they are attached represent a fused furan or thiophene ring. Moreover, it is to be understood that when Z is $Z^4$ or $Z^5$, the Z group can be attached in either of two possible ways. Thus, for example, when X and Y are at C-5 and C-6 and they are $Z^5$, the formula IV embraces both of the following formulae:

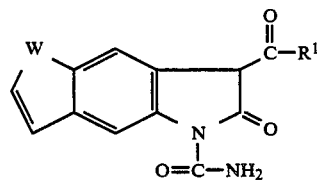

and

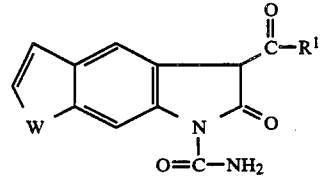

The compounds of formula III are prepared from the appropriate 2-oxindoles of formula I by the two-step sequence shown above. The required 2-oxindoles (R=H) are prepared by methods known to those skilled in the art. The following references describe preparation of various 2-oxindoles: "The Chemistry of Heterocyclic Compounds", Indoles, Part Two, Edited by Houlihan, Wiley-Interscience, N.Y., pp. 142–143, (1973); "Rodd's Chemistry of Carbon Compounds", Second Edition, Edited by S. Coffey; Vol. IV-A, Elsevier Scientific Publishing Company, pp. 448–450, (1973); Walker, J. Am. Chem. Soc , 77, 3844–3850 (1955); Wright et al., J. Am. Chem. Soc., 78, 221–224 (1956); McEvoy et al., J. Org. Chem. 38, 3350 (1973); Gassman et al., J. Org. Chem., 42, 1340 (1977); Beckett et al., Tetrahedron 24, 6093 (1968); Protiva et al., Coll Czech. Chem. Comm. 44, 2108 (1979); and U.S. Pat. Nos. 3,882,236; 4,006,161 and 4,160,032. Additionally, preparations of representative substituted 2-oxindoles are presented herein.

The starting materials of formula I wherein R is $-CO-R^1$ wherein $R^1$ is as defined above are prepared by acylating the appropriate compound of formula I wherein R is hydrogen by methods known to those skilled in the art. For example, the acyl moiety $-CO-R^1$ is attached by reacting a compound of the formula I with an activated derivative of the appropriate acid of the formula $R^1-C(=O)-OH$, in a lower-alkanol solvent (e.g. ethanol), in the presence of an alkali metal salt of the lower-alkanol solvent (e.g. sodium ethoxide), according to standard procedures. Typical derivatives of the acid of the formula $R^1-C(=O)OH$ which can be used include acid chlorides, acid anhydrides of the formula $R^1-C(=O)-O-C(-$ =O)—R¹, R¹—C(=O)—O—C(=O)—R³ and R¹—C(=O)—O—C(=O)—OR⁴, and simple alkyl esters of the formula R¹—C(=O)—OR⁴, wherein R³ is a bulky low molecular weight alkyl group such as t-butyl and R⁴ is a low molecular weight alkyl group. Usually, a small excess of the derivative of the acid of formula R¹—C(=O)—OH is used, and the alkoxide salt is usually present in an amount from one to two molar equivalents, based on said derivative of the acid of formula R¹—C(=O)OH. The reaction between the derivative of the acid of the formula R¹—C(=O)OH and the compound of formula I, wherein R is hydrogen, is usually started at 0° to 25° C., but it is then usual to heat the reaction mixture at a temperature in the range from 50° to 130° C., and preferably at about 80° C., to complete the reaction. Under these circumstances, reaction times of a few hours, e.g. two hours, up to a few days, e.g., two days, are commonly used. The reaction mixture is then cooled, diluted with an excess of water, and acidified. The product of formula I, wherein R is —CO—R¹ can then be recovered by filtration or by the standard procedure of solvent extraction.

The first step of the process of this invention, reaction of the appropriate 2-oxindole with chlorosulfonyl isocyanate, is conducted in a reaction-inert solvent medium; i.e., a solvent which does not react with the chlorosulfonyl isocyanate or the 2-oxindole-1-chlorosulfonylamide product of formula II. Said solvent need not bring about complete solution of the reactants. Representative solvents are dialkyl ethers such as diethyl ether; diisopropyl ether; aromatic hydrocarbons such as benzene, xylene and toluene; chlorinated hydrocarbons such as methylene chloride and chloroform; and acetonitrile.

The reaction is generally conducted at temperatures ranging from −20° C. to the reflux temperature of the solvent used. In general, temperatures of from 25° C. to 110° C. are favored. Temperatures down to −70° C., can be used if desired. However, temperatures below 0° C. are generally avoided for practical reasons.

The 2-oxindole and chlorosulfonyl isocyanate are generally reacted in molar proportions ranging from equimolar to 30% excess of chlorosulfonyl isocyanate, i.e., 1:1 to 1:1.3. Larger excesses of chlorosulfonyl isocyanate appear to afford no advantages and are not used for reasons of economy.

The thus-produced chlorosulfonamide derivatives of formula II can be isolated, if desired, or can be converted directly in the same reaction vessel without isolation to formula III compounds. Isolation of the intermediate chlorosulfonamido compounds of formula II is achieved by procedures known to those skilled in the art; e.g. by filtration, evaporation of solvent or extraction.

The second step of the process, hydrolysis of the chlorosulfonamido derivatives (formula II) is carried out by treating the formula II compounds, with or without isolation thereof, with water, aqueous acid or aqueous base. Water alone is generally favored as the hydrolyzing agent even in instances wherein the hydrolysis step involves a two phase system. The rate of hydrolysis is sufficiently rapid as to overcome any solubility problems of reactants. Additionally, from the standpoint of large scale reactions, the use of water alone is more economical than are the other hydrolysis methods.

The use of an aqueous inorganic or organic acid as hydrolyzing agent sometimes overcomes the development of two phase reaction systems. This is often the case when aqueous acetic acid is used. The amount of acid is not critical to the hydrolysis step. It can range from less than equimolar quantities to greater than equimolar quantities. Also not critical is the concentration of the acid used. In general, when aqueous acid is used for the hydrolysis step, from about 0.1 mole of acid per mole of formula II compound to up to 3 moles of acid per mole of formula II compound. Acid concentrations of from about 1 molar to 6 molar are generally used for ease of handling. The use of aqueous acid is often resorted to when the formula II intermediate is isolated and a single phase hydrolysis mixture is desired. Representative acids are hydrochloric, sulfuric, phosphoric, acetic, formic, citric and benzoic acids.

The compounds of formula IV are prepared from the appropriate 2-oxindole-1-carboxamide compound of the formula III, wherein R is hydrogen, and X and Y are as previously defined. This is accomplished by attaching the substituent —C(=O)—R¹ to the 3-position of the 2-oxindole nucleus. The —C(=O)—R¹ substituent is attached by reacting said compound of the formula III with an activated derivative of a carboxylic acid of the formula R¹—C(=O)OH. The reaction is carried out by treating said compound of formula III in an inert solvent with one molar equivalent, or a slight excess, of an activated derivative of a compound of formula R¹—C(=O)OH, in the presence of from one to four equivalents of a basic agent. An inert solvent is one which will dissolve at least one of the reactants, and will not adversely interact with either of the reactants or the product. However, in practice, a polar, aprotic solvent, such as N,N-dimethylformamide, N,N-dimethylacetamide, N-methylpyrrolidone or dimethyl sulfoxide, is commonly used. Conventional methods for activating the acid of formula R¹—C(=O)OH are used. For example, acid halides, e.g., acid chlorides, symmetrical acid anhydrides, R¹—C(=O)—O—C(=O)—R¹, mixed acid anhydrides with a hindered low-molecular weight carboxylic acid, R¹—C(=O)—O—C(=O)—R³, where R³ is a bulky lower-alkyl group such as t-butyl, and mixed carboxylic-carbonic anhydrides, R¹—C(=O)—O—C(=O)—OR⁴, wherein R⁴ is a low-molecular weight alkyl group, can all be used. In addition, N-hydroxyimide esters (such as N-hydroxysuccinimide and N-hydroxyphthalimide esters), 4-nitrophenyl esters, thiol esters (such as thiol phenyl esters) and 2,4,5-trichlorophenyl esters, and the like, can be used. Moreover, in those cases in which R¹ is a heteroaryl group (e.g., furyl), simple alkyl esters of the formula R¹—C(=O)—O—R⁴, where R⁴ is a low-molecular weight alkyl group (e.g., ethyl), can sometimes be used as the activated derivative of the acid of formula R¹—C(=O)—OH when attaching the —C(=O)—R¹ substituent to the 3-position of the 2-oxindole compound of formula III, wherein R is hydrogen.

A wide variety of basic agents can be used in the reaction between a compound of formula III, wherein R is hydrogen and the activated derivative of the acid of the formula R¹—C(=O)OH. However, preferred basic agents are tertiary amines, such as trimethylamine, triethylamine, tributylamine, N-methylmorpholine, N-methylpiperidine and 4-(N,N-dimethylamino)pyridine.

The reaction between a compound of the formula III, wherein R is hydrogen, and the activated derivative of the acid of formula R¹—C(=O)—OH is usually carried out in the temperature range from −10° to 25° C. Reaction times of from 30 minutes to a few hours are common. At the end of the reaction, the reaction medium is usually diluted with water and acidified, and then the product can be recovered by filtration. It can be purified by standard methods, such as recrystallization.

The analgesic activity of compounds of formula IV has been demonstrated in mice by showing blockade of the abdominal stretching induced by administration of 2-phenyl-1,4-benzoquinone (PBQ). The method used was based on that of Siegmund et al., *Proc. Soc. Exp. Biol. Med.*, 95: 729–731, 1957, as adapted for high throughput (see further Milne and Twomey, *Agents and Actions*, 10: 31–37, 1980). The mice used in these experiments were Carworth males, albino CF-1 strain, weighing 18-20 g. All mice were fasted overnight prior to drug administration and testing.

The compounds of formula IV were dissolved or suspended in a vehicle consisting of ethanol (5%), emulphor 620 (a mixture of polyoxyethylene fatty acid esters, 5%) and saline (90%). This vehicle also served as control. Doses were on a logarithmic scale (i.e., ... 0.32, 1.0, 3.2, 10, 32 ... mg/kg). The route of administration was oral, with concentrations varied to allow a constant injection volume of 10 ml/kg of mouse. The aforesaid method of Milne and Twomey was used to determine efficacy and potency. Mice were treated with compounds orally, and one hour later received PBQ, 2 mg/kg intraperitoneally. Individual mice were then immediately placed in a warmed lucite chamber, and, starting five minutes after PBQ administration, the number of abdominal constrictions during the subsequent 5 minutes was recorded. The degree of analgesic protection (% MPE) was calculated on the basis of suppression of abdominal constriction relative to counts from concurrent control animals run on the same day. At least four such determinations ($N \geq 5$) provided dose-response data for generation of an $MPE_{50}$, the best estimate of the dose that reduces abdominal constriction of 50% of control levels.

The antiinflammatory activity of compounds of formula IV has been demonstrated in rats by a method based on the standard carrageenin-induced rat-foot edema test. (Winter et al., *Proc. Soc. Exp. Biol. Med.*, 111: 544, 1963).

Unanesthetized, adult, male, albino rats of 150 g to 190 g body weight were numbered, weighed, and an ink mark placed on the right lateral malleolus. Each paw was immersed in mercury exactly to the ink mark. The mercury was contained a glass cylinder, connected to a Statham Pressure Transducer. The output from the transducer was fed through a control unit to a microvoltameter. The volume of mercury displaced by the immersed paw was read. Drugs were given by gavage. One hour after drug administration, edema was induced by injection of 0.05 ml of 1% solution of carrageenin into the plantar tissue of the marked paws. Immediately thereafter, the volume of the injected foot was measured. The increase in foot volume 3 hours after the injection of carrageenin constitutes the individual response.

The analgesic activity of compounds of formula IV makes them useful for acute administration to mammals, including humans, for the control of pain, e.g., postoperative pain and the pain of trauma. The antiinflammatory activity of said compounds makes them useful for chronic administration to mammals, including humans, for the control of inflammatory diseases, such as the arthritides, especially rheumatoid arthritis.

When a compound of formula IV is to be used for either of said purposes, it can be administered to a mammalian subject alone, or, preferably, in combination with pharmaceutically-acceptable carriers or diluents in a pharmaceutical composition, according to standard pharmaceutical practice via the oral or parenteral (includes intravenous, intramuscular, intraperitoneal, subcutaneous and topical) route.

In a pharmaceutical composition comprising a compound of formula IV, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use, said formula IV compound, can be administered in the form of tablets or capsules, or as an aqueous solution or suspension. Commonly used carriers for tablets include lactose and corn starch. Lubricating agents, such as magnesium stearate, are commonly added. Useful diluents for capsule dosage forms are lactose and dried corn starch. When aqueous suspensions are required for oral use, the active ingredient is combined with emulsifiying and suspending agents. If desired, certain sweetening and/or flavoring agents can be added. For intramuscular, intraperitoneal, subcutaneous and intravenous use, sterile solutions of the active ingredient are usually prepared, and the pH of said solutions suitably adjusted and buffered. For intravenous use, the total concentration of solutes should be controlled to render the preparation isotonic.

When a compound of formula IV is used in a human subject, the daily dosage, normally determined by the prescribing physician, will vary according to the age, weight and response of the individual patient, as well as the severity of the patient's symptoms However, for acute administration to relieve pain, an effective dose in most instances will be 0.1 to 1.0 g as needed (e.g., every four to six hours) For chronic administration as an antiinflammatory agent, in most instances an effective dose will be from 0.5 to 3.0 g per day, in single or divided doses. On the other hand, it may be necessary to use dosages outside these limits in some cases.

The following examples and preparations are provided solely for the purpose of illustrating the present invention No attempt was made to optimize the yield of said examples and preparations

EXAMPLE 1

2-Oxindole-1-Carboxamide

Chlorosulfonyl isocyanate (1.20 g, 8.4 mmoles) was added to a mixture of 2-oxindole (0.94 g, 7.1 mmole) in ether (30 ml) and the reaction stirred at room temperature for 20 hours. The ether was removed under vacuum and the residue treated with water (10 ml) and 1N HCl (10 ml). Ethyl acetate (125 ml) was added and the mixture stirred for one hour. The ethyl acetate phase was separated, washed with 1N HCl (1×50 ml), brine (2×100 ml) and dried (MgSO$_4$). Concentration afforded 0.97 g (77%) of crude product. Recrystallization from ethanol gave 0.18 g; m.p. 178°–180° C.

EXAMPLE 2

2-Oxindole-1-Carboxamide

A mixture of 2-oxindole (5.86 g, 44.0 mmoles) in toluene (160 ml) was azeotroped for one hour to dry the toluene. Then, chlorosulfonyl isocyanate (7.47 g, 52.8 mmole) was added. Hydrogen chloride was immediately evolved. The mixture was stirred and refluxed for 15 minutes and then cooled to room temperature. Water (50 ml) was added to the cooled mixture (some HCl was initially evolved) and the mixture stirred for 1.5 hours. The solid which formed was collected by filtration and dried (4.10 g). The filtrate was extracted with ethyl acetate (100 ml), the resulting extract washed with brine (2×100 ml) and dried (MgSO4). Evaporation of the extract under reduced pressure gave 4.16 g of solid. The combined solids were recrystallized by dissolution in acetonitrile (200 ml) followed by concentration of the solution under reduced pressure to about 75 ml. The small amount of amorphous material which separated was filtered off, the filtrate decolorized and concentrated under reduced pressure to about 50 ml volume, then seeded. The dark red crystals which separated were filtered and dried (3.0 g; 38%). It was identical to the product of Example 1.

EXAMPLE 3

2-Oxindole-1-Carboxamide

To a slurry of 2-oxindole (13.3 g, 0.10 mole) in toluene (150 ml) was added chlorosulfonyl isocyanate (15.6 g, 0.11 mole) and the reaction mixture heated on a steam bath for ten minutes (a clear solution formed within about three minutes followed almost immediately by formation of a precipitate). It was then cooled in in ice bath for 30 minutes, the solid filtered off and air dried.

The thus obtained chlorosulfonamido intermediate was added to a 2:1 mixture of acetic acid/water (240 ml) and the resulting slurry heated on a steam bath for ten minutes. It was cooled in an ice bath and the off white solid which formed filtered off and air dried. Concentration of the mother liquor to a slush and filtration thereof gave 1.2 g of product. The combined solids was recrystallized from about 250 ml of ethanol; yield=11.48 g (65%). It was identical to the Example 1 product.

EXAMPLE 4

6-Fluoro-5-Methyl-2-Oxindole-1-Carboxamide

Following the procedure of Example 2, the title compound was prepared from 6-fluoro-5-methyl-2-oxindole (1.0 g, 6.0 mmole), chlorosulfonyl isocyanate (1.03 g, 7.3 mmole), toluene (30 ml). Water (5 ml) was used for the hydrolysis step. Yield=0.58 g, 46%. M.P. 200°–203° C.

Analysis Calcd. for $C_{10}H_9N_2O_2F$: C, 57.69; H, 4.36; N, 13.46. Found: C, 57.02; H, 4.41; N, 12.85.

A sample of the chlorosulfonamide intermediate was removed prior to hydrolysis and subjected to mass spectrum analysis for exact mass determination: $C_{10}H_8N_2O_4SCl$: 307. 9848.

EXAMPLES 5–13

Substituted-2-Oxindole-1-Carboxamides

The following compounds are prepared according to the procedure of Example 3 from appropriately substituted-2-oxindoles.

| EX-AM-PLE | 2-Oxindole X | Y | g. | CSI g. | Solvent ml. | Intermediate g. | MP (°C.) | Hydrolysis ml HOAC/H2O | 2-Oxindole-1-Carboxamide Product g. | Yield % | MP (°C.) | Analysis Calcd. C | H | N | Found C | H | N |
|---|---|---|---|---|---|---|---|---|---|---|---|---|---|---|---|---|---|
| 5 | 5-CH3 | H | 11.51 | 12.2 | 150 | 16 | | 120/160 | 7.3 | 49 | 215–6 (dec) | | | | | | |
| 6 | 5-OCH3 | H | 8.15 | 7.78 | 100 | 8.4 | | 80/40 | 7.3 | 70 | 191–2 | | | | | | |
| 7 | 4-Cl | H | 5.03 | 4.67 | 85 | | 149–50 | 45/25 | 3.64 | 58 | 201–2[a] | 51.32 | 3.35 | 13.30 | 51.04 | 3.26 | 13.24 |
| 8 | 5-Cl | H | 10.0 | 9.3 | 200 | 15.8 | 163 | 50/5 | 9.8 | 46.8 | 211 (dec) | 51.32 | 3.35 | 13.30 | 51.14 | 3.48 | 13.21 |
| 9 | 6-Cl | H | 4.18 | 3.89 | 85 | | 165–6 (dec) | 41/21 | 4.09 | 78 | 221–2 (dec) | 51.32 | 3.35 | 13.30 | 51.07 | 3.30 | 13.31 |
| 10 | 5-F | H | 10.0 | 10.3 | 100 | 16 | | 50/100 | 6.7 | 52.3 | 198[b] | 55.67 | 3.64 | 14.43 | 56.25 | 3.79 | 14.53 |
| 11 | 5-CF3 | H | 4.4 | 3.4 | 45 | 6.5 | | 20/40 | 3.4 | 63.3 | 214.5[b] | 49.19 | 2.89 | 11.48 | 48.90 | 3.05 | 11.50 |
| 12 | 4-CH3 | 5-CH3 | 4.8 | 4.7 | 45 | 8.8 | | 25/50 | 4.08 | 66.6 | 222 (dec) | 64.69 | 5.92 | 13.72 | 64.57 | 5.94 | 13.64 |
| 13 | 5-CH3 | 6-CH3 | 1.6 | 1.6 | 15 | 2.8 | | 8/17 | 1.3 | 63.7 | 214.5[c] | 64.69 | 5.92 | 13.72 | 64.52 | 6.67 | 13.68 |

[a]Recrystallized from ethanol
[b]Recrystallized from acetonitrile
[c]Recrystallized from acetic acid

EXAMPLE 14

5,6-Methylenedioxy-2-oxindole-1-carboxamide 5,6-Methylenedioxy-2-oxindole-1-carboxamide was prepared by reaction of 5,6-methylenedioxy-2-oxindole with chlorosulfonyl isocyanate, followed by hydrolysis, using the procedure of Example 3. The product melted at 237°–238° C. (dec.) after recrystallization from acetic acid.

EXAMPLE 15

By reaction of the appropriate 2-oxindole with chlorosulfonyl isocyanate, followed by hydrolysis, using the procedure of Example 3, the following compounds can be prepared.

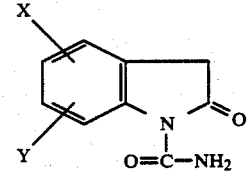

| X | Y |
|---|---|
| 5-n-OC4H9 | H |
| 5-OC2H5 | H |
| 7-Cl | H |
| 5-n-C4H9 | H |
| 5-n-SC4H9 | H |
| 6-OCH3 | H |
| 6-n-SC4H9 | H |
| 5-CH(CH3)2 | H |
| 6-n-C4H9SO | H |
| 6-n-C4H9SO2 | H |
| H | 5-Br |
| 6-n-C3H7CO | H |

-continued

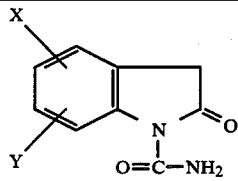

| X | Y |
|---|---|
| 5-(CH₃)₂CHCONH | H |
| 5-SO₂N(CH₃)₂ | H |
| 5-SO₂N(n-C₃H₇)₂ | H |

EXAMPLE 16

By reaction of the appropriate 2-oxindole with chlorosulfonyl isocyanate, followed by hydrolysis, using the procedure of Example 3, the following tricyclic compounds can be prepared:

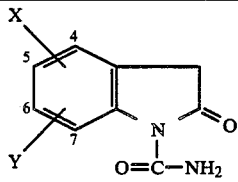

X and Y*

4-CH₂—CH₂—CH₂—5
5-CH₂—CH₂—CH₂—6
6-CH₂—CH₂—CH₂—CH₂—7
5-CH=CH—CH=CH—6
5-O—CH₂—CH₂—6
5-CH₂—CH₂—O—6
5-S—CH₂—CH₂—6
5-O—CH=CH—6
5-S—CH=CH—6
5-CH=CH—S—6

*In this column, the numeral to the left of the formula indicates the point attachment of that end of the formula to the 2-oxindole nucleus and the numeral to the right indicates the point of attachment of that end of the formula to the 2-oxindole nucleus.

EXAMPLE 17

6-Methylthio-2-Oxindole-1-Carboxamide

Chlorosulfonyl isocyanate (5.66 g, 0.04 mole) was added to a slurry of 6-methylthio-2-oxindole (6.0 g, 0.033 mole) in acetonitrile (60 ml) at 5° to 10° C. The reaction mixture was stirred for one hour. Water (100 ml) was then added to said mixture with good stirring for ten minutes. The aqueous solution was extracted with ethyl acetate (600 ml), washed successively with water and brine, dried (MgSO₄) and evaporated under reduced pressure to give a gray solid which was recrystallized from acetonitrile. Yield=3.0 g. An additional 0.71 g of product was obtained from the mother liquor. Total yield=3.71 g (50.6%); m.p. 176°–179° C.

EXAMPLE 18

5,6-Dimethoxy-2-Oxindole-1-Carboxamide

Following the procedure of Example 17 the title compound was prepared from 5,6-dimethoxy-2-oxindole (8.0, 0.042 mole), chlorosulfonyl isocyanate (7.08 g, 0.05 mole) and acetonitrile (75 ml). The crude product obtained upon evaporation of the ethyl acetate extract was recrystallized from acetonitrile/acetic acid (1:1). Yield=6.02 g (60%); m.p. 206.5°–209° C.

Similarly, 5,6-methylenedioxy-2-oxindole-1-carboxamide is prepared from 5,6-methylenedioxy-2-oxindole.

EXAMPLE 19

6-Trifluoromethyl-2-Oxindole-1-Carboxamide

To a slurry of 6-trifluoromethyl-2-oxindole (8.0 g, 0.04 mole) in acetonitrile (80 ml) was added chlorosulfonyl isocyanate (6.65 g, 0.047 mole) and the mixture stirred for 45 minutes. Water (100 ml) was then added and the aqueous mixture stirred for one hour. The precipitate which formed was filtered off and recrystallized from acetonitrile to give 0.92 g of title product. Extraction of the filtration from the aqueous reaction mixture with ethyl acetate (300 ml) followed by drying the extract over MgSO₄ and then evaporating it under reduced pressure gave additional product. Recrystallization from acetonitrile gave additional (2.2 g) product.

Additional product (1.85 g) was recovered by combining the mother liquors from the acetonitrile recrystallizations and concentrating same under reduced pressure. Total yield=4.97 g (51%) m.p. 207.5°–210° C.

EXAMPLES 20–25

Repetition of the procedure of Example 19 but using the appropriate substituted 2-oxindole afforded the following compounds.

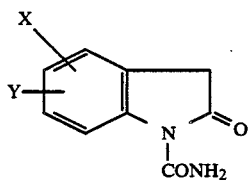

| EXAMPLE | 2-Oxindole X | Y | g. | CSI g. | Solvent ml. | Intermediate MP (°C.) | Hydrolysis Agent-Water (ml.) | 2-Oxindole-1-Carboxamide Product g. | % | MP (°C.) |
|---|---|---|---|---|---|---|---|---|---|---|
| 20 | 4-SCH₃ | H | 2.25 | 2.26 | 25 | | 20 | 1.62 | 56 | 181–4 |
| 21 | 6-F | H | 1.06 | 0.99 | 15 | 141.5–143° | 15 | 1.21 | 94.5 | 191.5–194 |
| 22 | 6-Br | H | 3.75 | 2.97 | 40 | 158–161° | 40 | 2.50 | 58 | 205–8 |
| 23 | 5-NO₂ | H | 1.1 | 1.13 | 30 | 232–235° | 5 | 0.52 | 38.5 | 201–5 |
| 24 | 5-F | 6-Cl | 1.59 | 1.42 | 55$^a$ | | 20 | 1.02$^b$ | 52$^c$ | 229–31 |

-continued

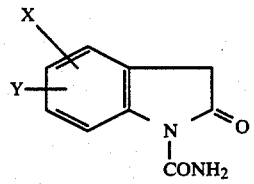

| EXAMPLE | 2-Oxindole X | Y | CSI g. | Solvent ml. | Intermediate MP (°C.) | Hydrolysis Agent-Water (ml.) | 2-Oxindole-1-Carboxamide Product g. | Yield % | MP (°C.) |
|---|---|---|---|---|---|---|---|---|---|
| 25 | 5-F | 6-F | 3.0 | 2.98 | 13 | | 15 | 2.60 | 72 | 198–201 |

[a]toluene used as solvent
[b]NMR shows the isomeric 4-chloro-5-fluoro-2-oxindole-1-carboxamide also produced. (starting material a mixture of isomers).
[c]Evaporation of toluene solvent gave an additional 0.59 g. for 84% yield.

EXAMPLE 26
3-(2-Furoyl)-6-Fluoro-2-Oxindole-1-Carboxamide

Following substantially the procedure of Example 19, the title was prepared in 17% yield from: 3-(2-furoyl)-6-fluoro-2-oxindole (0.30 g, 1.2 mmole), chlorosulfonyl isocyanate (0.20 g, 1.4 mmole), acetonitrile (15 ml), and water (10 ml), Yield=0,060 g; m.p.=231°–235° C.

In like manner, the 3-acyl-2-oxindoles in Tables I and II below are converted to the corresponding 3-acyl-2-oxindole-1-carboxamides.

TABLE I

| X | Y | $R^1$ | X | Y | $R^1$ |
|---|---|---|---|---|---|
| H | H | 2-thienyl | H | 5-$CF_3$ | phenoxymethyl |
| H | H | 2-thienylmethyl | H | 5-Cl | phenyl |
| H | H | phenoxymethyl | H | 5-$CH_3$ | phenyl |
| H | H | 3-furyl | H | 5-Cl | cyclobutyl |
| H | 5-Cl | 2-thienyl | H | 6-Cl | cyclopentyl |
| H | 5-Cl | 2-furyl | H | 6-Br | 2-furyl |
| H | 5-Cl | 3-thienyl | H | 5-$NO_2$ | benzyl |
| H | 6-Cl | 3-thienylmethyl | H | 5-$NO_2$ | 2-thienyl |
| H | 5-$CF_3$ | 2-thienyl | H | 5-O—n-$C_4H_9$ | 2-furyl |
| H | 6-$CF_3$ | 2-furylmethyl | H | 6-F | n-hexyl |
| H | 5-Cl | methyl | H | 5-F | cycloheptyl |
| H | 5-F | isopropyl | 5-$CH_3$ | 6-$CH_3$ | 3-(phenyl)-propyl |
| H | 5-F | cyclohexyl | H | 5-$NO_2$ | (3-fluorophenoxy)methyl |
| H | H | 4-chlorophenoxymethyl | H | 6-$OCH_3$ | 3-(phenoxy)-propyl |
| H | 5-Cl | cyclopropyl | H | 5-$CH_3$ | 4-bromophenyl |
| H | 6-F | bicyclo[2.2.1]-heptan-2-yl | H | 5-Cl | 2-fluoro-phenyl |
| H | 4-Cl | 2-thienyl | H | 6-O—n-$C_4H_9$ | (4-chloro-phenoxy)methyl |
| 5-$CH_3$ | 6-F | 2-furyl | 5-F | 6-Cl | (4-bromophenyl)-methyl |
| 5-$OCH_3$ | 6-$OCH_3$ | methyl | H | 6-Cl | (2-methylphenoxy)-methyl |
| H | 5-$CF_3$ | isopropyl | H | 4-$SCH_3$ | (4-n-butoxy-phenoxy)methyl |
| H | H | 4-chlorophenyl | H | 6-$SCH_3$ | 3-methyl-2-furyl |
| H | H | 4-methylphenyl | H | 7-Cl | 5-propyl-2-furyl |
| H | H | benzyl | H | 5-i-$C_3H_7$ | thienyl |
| H | H | 1-(phenyl)ethyl | H | 5-$OC_2H_5$ | 1-(2-furyl)-ethyl |
| H | 5-$CF_3$ | 4-chlorophenyl | H | 7-Cl | 3-(2-furyl)-propyl |
| H | 6-$SCH_3$ | 2-thienylmethyl | H | 5-$NO_2$ | 3-(3-thienyl)-propyl |
| H | 5-F | 2-thienyl | H | 5-F | methyl |
| H | 6-F | 2-thienyl | H | 6-Cl | 2-thienyl- |

TABLE I-continued

[Structure: 2-oxindole with X, Y substituents and CO-R¹ at 3-position]

| X | Y | R¹ | X | Y | R¹ |
|---|---|---|---|---|---|
| | | methyl | | | |

TABLE II

[Structure: 2-oxindole with X at 4/5, Y at 6/7 positions, CO-R¹ at 3-position]

| X and Y* | R¹ |
|---|---|
| 4-CH₂—CH₂—CH₂—5 | 2-furyl |
| 5-CH₂—CH₂—CH₂—6 | 2-thienyl |
| 6-CH₂—CH₂—CH₂—CH₂—7 | 2-furyl |
| 5-CH=CH—CH=CH—6 | (2-thienyl)-methyl |
| 5-O—CH₂—CH₂—6 | 2-thienyl |
| 5-CH₂—CH₂—O—6 | 2-furyl |
| 5-S—CH₂—CH₂—6 | 2-thienyl |
| 5-O—CH=CH—6 | 2-furyl |
| 5-S—CH=CH—6 | (2-thienyl)-methyl |
| 5-CH=CH—S—6 | 2-furyl |

*In this column, the numeral to the left of the formula indicates the point attachment of that end of the formula to the 2-oxindole nucleus and the numeral to the right indicates the point of attachment of that end of the formula to the 2-oxindole nucleus.

EXAMPLE 27

Substituted 2-Oxindole-1-Chlorosulfonamides

The procedure of Example 17 was followed, using the appropriate substituted-2-oxindole as reactant. Prior to the hydrolysis step, the intermediate chlorosulfonyl derivative was recovered by filtration, if a solid was present; or by evaporation from a small volume of the reaction mixture if no precipitation formed. A sample of the thus obtained intermediate was then subjected to exact mass determination.

[Structure: 2-oxindole with X, Y substituents and O=C—NH—SO₂Cl on N]

| 2-Oxindole | | CSI | ml Sol- | Intermediate | |
|---|---|---|---|---|---|
| X | Y | g. | g. | vent | Formula | Exact Mass |
| 6-F | H | 1.5 | 1.70 | 15 | $C_9H_6N_2O_4FSCl$ | 291.9721 |
| 6-CF₃ | H | 0.5 | 0.35 | 10$^a$ | $C_{10}H_6N_2O_4F_3SCl$ | 341.3693 |
| 5-F | 6-Cl | 1.59 | 1.42 | 55$^a$ | $C_9H_6N_2O_4FSCl_2$ | 326.9340 |
| 5-NO₂ | H | 1.75 | 0.35 | 55$^a$ | $C_9H_6H_3O_6SCl$ | 318.9675 |
| 6-Br | H | 0.40 | 0.31 | 5$^a$ | $C_9H_6N_2O_4SBrCl$ | 351.8863 |
| 5-OCH₃ | 6-OCH₃ | 1.0 | 0.85 | 12 | $C_{11}H_{11}N_2O_6SCl$ | 344.0034 |
| 6-SCH₃ | H | 0.20 | 0.18 | 3$^a$ | $C_{10}H_9N_2O_4S_2Cl$ | 319.9636 |
| 4-SCH₃ | H | 0.20 | 0.18 | 3$^a$ | $C_{10}H_9N_2O_4S_2Cl$ | 319.9696 |

-continued

[Structure: 2-oxindole with X, Y substituents and O=C—NH—SO₂Cl on N]

| 2-Oxindole | | CSI | ml Sol- | Intermediate | |
|---|---|---|---|---|---|
| X | Y | g. | g. | vent | Formula | Exact Mass |
| 6-F | 5-CH₃ | 0.16 | 0.14 | 10$^a$ | $C_{10}H_8N_2O_4FClS$ | 307.9848 |

$^a$ = toluene used as solvent

EXAMPLE 28

6-Phenyl-2-oxindole-1-carboxamide

To 4.5 g. (21.5 mmole) of 6-phenyl-2-oxindole in a mixture of 100 ml. of toluene and 25 ml. of tetrahydrofuran was added, with stirring, at 5° C., 2.2 ml. (25.8 mmole) of chlorosulfonyl isocyanate. Stirring was continued for 1 hour at 0°–5° C. and then 100 ml. of water was added. The solid was recovered by filtration and added to a mixture of 40 ml. of glacial acetic acid and 80 ml. of water. The resulting mixture was heated at 100° C. for 1 hour, cooled and filtered. The residue was dried to give 3.1 g. of the title compound, mp. 188°–189° C.

EXAMPLE 29

5-Benzoyl-2-oxindole-1-carboxamide

A mixture of 10.1 g. (42 mmole) of 5-benzoyl-2-oxindole, 4.4 ml. (51 mmole) of chlorosulfonyl isocyanate and 300 ml. of tetrahydrofuran was stirred at room temperature for 6 hours, and then the solvent was removed by evaporation in vacuo. The residue was added to 150 ml. of glacial acetic acid and 300 ml. of water and the resulting mixture was heated under reflux for 2 hours. The reaction mixture was cooled and the supernatant liquid was removed by decantation. The remaining gummy residue was triturated under acetonitrile to give a solid which was recovered by filtration and then recrystallized from a 1:1 mixture of n-propanol and acetonitrile. This gave 4.1 g. of the title compound as a solid, mp. 210°–211° C.

EXAMPLE 30

Reaction of 5-acetyl-2-oxindole and 5-(2-thenoyl)-2-oxindole with chlorosulfonyl isocyanate, followed by hydrolysis with aqueous acetic acid, substantially according to the procedure of Example 29, afforded the following compounds:

5-acetyl-2-oxindole-1-carboxamide, 34% yield, mp 225° C. (dec.) (from CH₃CN) and
5-(2-thenoyl)-2-oxindole-1-carboxamide, 51% yield, mp 200° C. (dec.) (from CH₃OH/CH₃CN),
respectively.

EXAMPLE 31

3-(2-Thenoyl)-5-chloro-2-oxindole-1-carboxamide

To a stirred slurry of 1.5 g. (5.4 mmole) of 3-(2-thenoyl)-5-chloro-2-oxindole in 15 ml. of dry acetonitrile was added 0.52 ml. (5.9 mmole) of chlorosulfonyl isocyanate, and the reaction mixture was stirred at room temperature for 2 hours. A small sample was removed, filtered and evaporated in vacuo to give a small sample of N-chlorosulfonyl-3-(2- thenoyl)-5-chloro-2-oxindole-1-carboxamide, mp 166°–169° C. To the remainder of the reaction mixture, 30 ml. of water was added slowly with stirring and stirring was continued for 1 hour. The reaction mixture was then poured into 50 ml. of 1N hydrochloric acid containing ice chips, and the resulting mixture was stirred for 20 minutes. The yellow solid was recovered by filtration, washed with water and diisopropyl ether and recrystallized from glacial acetic acid to give 200 mg. of a first crop of the title compound, mp 213°–215° C. The mother liquors from which the first crop had been recovered deposited a further yellow solid. The latter solid was recovered by filtration to give 470 mg. of a second crop of the title compound. The second crop was recrystallized from glacial acetic acid and combined with the first crop and recrystallized from glacial acetic acid. This gave 280 mg. of the title compound, mp 232°–234° C.

PREPARATION 1

5-Chloro-2-oxindole

To a stirred slurry of 100 g (0.55 mol) of 5-chloroisatin in 930 ml of ethanol was added 40 ml (0.826 mol) of hydrazine hydrate, resulting in a red solution. The solution was heated under reflux for 3.5 hours, during which time a precipitate appeared. The reaction mixture was stirred overnight, and then the precipitate was recovered by filtration to give 5-chloro-3-hydrazono-2-oxindole as a yellow solid, which was dried in a vacuum oven. The dried solid weighed 105.4 g.

The dried solid was then added portionwise, during 10 minutes, to a solution of 125.1 g of sodium ethoxide in 900 ml of absolute ethanol. The resultant solution was heated under reflux for 10 minutes and then it was concentrated in vacuo to a gummy solid. The gummy solid was dissolved in 400 ml of water and the aqueous solution thus obtained was decolorized with activated carbon and then poured into a mixture of 1 liter of water and 180 ml of concentrated hydrochloric acid containing ice chips. A tan solid precipitated and it was collected by filtration and washed thoroughly with water. The solid was dried and then it was washed with diethyl ether. Finally it was recrystallized from ethanol to give 48.9 g of the title compound, mp 193°–195° C. (dec).

In an analogous fashion, 5-methylisatin was converted into 5-methyl-2-oxindole by treatment with hydrazine hydrate followed sodium ethoxide in ethanol. The product melted at 173°–174° C.

PREPARATION 2

4,5-Dimethyl-2-oxindole and 5,6-dimethyl-2-oxindole 3,4-Dimethylaniline was converted into 3,4-dimethylisonitrosoacetanilide by reaction with chloral hydrate and hydroxylamine, using the method described in "Organic Syntheses," Collective Volume I, page 327. The 3,4-dimethyl-isonitrosoacetanilide was cyclized with sulfuric acid, according to the method of Baker et al., *Journal of Organic Chemistry*, 17, 149 (1952), to give 4,5-dimethylisatin (m.p. 225°–226° C.) and 5,6-dimethylisatin (m.p. 217°–218° C.).

4,5-Dimethylisatin was converted into 4,5-dimethyl-2-oxindole, m.p. 245.5°–247.5° C., by treatment with hydrazine hydrate, followed by sodium ethoxide in ethanol, substantially according to the procedure of Preparation 1.

In like manner, 5,6-dimethylisatin was converted into 5,6-dimethyl-2-oxindole, m.p. 196.5°–198° C., by treatment with hydrazine hydrate, followed by sodium ethoxide in ethanol, substantially according to the procedure of Preparation 1.

PREPARATION 3

4-Chloro-2-oxindole and 6-chloro-2-oxindole

A. Isonitroso-3-chloroacetanilide

To a stirred solution of 113.23 g (0.686 mol) of chloral hydrate in 2 liters of water was added 419 g (2.95 mol) of sodium sulfate, followed by a solution prepared from 89.25 g (0.70 mol) of 3-chloroaniline, 62 ml of concentrated hydrochloric acid and 500 ml of water. A thick precipitate formed. To the reaction mixture was then added, with stirring, a solution of 155 g (2.23 mol) of hydroxylamine in 500 ml of water. Stirring was continued and the reaction mixture was warmed slowly and it was maintained between 60° and 75° C. for approximately 6 hours, during which time an additional 1 liter of water had been added to facilitate stirring. The reaction mixture was then cooled and the precipitate was recovered by filtration. The wet solid was dried to give 136.1 g of isonitroso-3-chloroacetanilide.

B. 4-Chloroisatin and 6-chloroisatin

To 775 ml of concentrated sulfuric acid, preheated to 70° C., was added, with stirring, 136 g of isonitroso-3-chloroacetanilide at such a rate as to maintain the reaction medium at a temperature between 75° and 85° C. When all the solid had been added, the reaction mixture was heated at 90° C. for an additional 30 minutes. The reaction mixture was then cooled, and poured slowly onto ca 2 liters of ice, with stirring. Additional ice was added as necessary to maintain the temperature below room temperature. A red-orange precipitate formed which was recovered by filtration, washed with water and dried. The resultant solid was slurried in 2 liters of water, and then it was brought into solution by the addition of ca 700 ml of 3N sodium hydroxide. The solution was filtered, and then pH was adjusted to 8 with concentrated hydrochloric acid. At this point, 120 ml of a mixture of 80 parts water and 20 parts concentrated hydrochloric acid was added. The solid which precipitated was recovered by filtration, washed with water and dried to give 50 g of crude 4-chloroisatin. The filtrate from which the 4-chloroisatin had been recovered was further acidified to pH 0 using concentrated hydrochloric acid, whereupon a further precipitate formed. It was recovered by filtration, washed with water and dried, to give 43 g of crude 6-chloroisatin.

The crude 4-chloroisatin was recrystallized from acetic acid to give 43.3 g of material melting at 258°–259° C.

The crude 6-chloroisatin was recrystallized from acetic acid to give 36.2 g of material melting at 261°–262° C.

C. 4-Chloro-2-oxindole

To a stirred slurry of 43.3 g of 4-chloroisatin in 350 ml of ethanol was added 17.3 ml of hydrazine hydrate, and then the reaction mixture was heated under reflux for 2 hours. The reaction mixture was cooled, and the precipitate was recovered by filtration to give 43.5 g of 4-chloro-3-hydrazono-2-oxindole, mp 235°–236° C.

To a stirred solution of 22 g of sodium in 450 ml of anhydrous ethanol was added, portionwise, 43.5 g of 4-chloro-3-hydrazono-2-oxindole, and the resulting solution was heated under reflux for 30 minutes. The cooled solution was then concentrated to a gum, which was dissolved in 400 ml of water and decolorized using activated carbon. The resulting solution was poured onto a mixture of 1 liter of water and 45 ml of concentrated hydrochloric acid. The precipitate which formed was recovered by filtration, dried and recrystallized from ethanol, giving 22.4 g of 4-chloro-2-oxindole, mp 216°–218° C. (dec).

D. 6-Chloro-2-oxindole

Reaction of 36.2 g of 6-chloroisatin with hydrazine hydrate followed by sodium ethoxide in ethanol, substantially according to C above, afforded 14.2 g of 6-chloro-2-oxindole, mp 196°–198° C.

PREPARATION 4

5,6-Difluoro-2-oxindole

Reaction of 3,4-difluoroaniline with chloral hydrate and hydroxylamine followed cyclization with sulfuric acid, in a manner analogous to Parts A and B of Preparation 3, gave 5,6-difluoroisatin, which was reacted with hydrazine hydrate followed by sodium methoxide in ethanol, in a manner analogous to Preparation 1, to give the title compound, m.p. 187°–190° C.

PREPARATION 5

5-Fluoro-2-oxindole

To a stirred solution of 11.1 g (0.1 mol) of 4-fluoroaniline in 200 ml of dichloromethane, at −60° to −65° C., was added, dropwise, a solution of 10.8 g (0.1 mol) of t-butyl hypochlorite in 25 ml of dichloromethane. Stirring was continued for 10 minutes at −60° to −65° C., and then was added, dropwise, a solution of 13.4 g (0.1 mol) of ethyl 2-(methylthio)acetate in 25 ml of dichloromethane. Stirring was continued at −60° C. for 1 hour and then was added, dropwise, at −60° to −65° C., a solution of 11.1 g (0.11 mol) of triethylamine in 25 ml of dichloromethane. The cooling bath was removed, and when the reaction mixture had warmed to room temperature, 100 ml of water was added. The phases were separated, and the organic phase was washed with saturated sodium chloride solution, dried ($Na_2SO_4$) and evaporated in vacuo. The residue was dissolved in 350 ml of diethyl ether, to which was added 40 ml of 2N hydrochloric acid. This mixture was stirred at room temperature overnight. The phases were separated and the ether phase was washed with water, followed by saturated sodium chloride. The dried ($Na_2SO_4$) ether phase was evaporated in vacuo to give 17 g of an orange-brown solid which was triturated under isopropyl ether. The solid was then recrystallized form ethanol, to give 5.58 g of 5-fluoro-3-methylthio-2-oxindole, mp 151.5°–152.5° C.

Analysis: Calcd for $C_9H_8ONFS$: C, 54.80; H, 4.09; N, 7.10%. Found: C, 54.74; H, 4.11; N, 7.11%.

A sample of the above 5-fluoro-3-methylthio-2-oxindole (986 mg, 5.0 mmol) was added to 2 teaspoonsful of Raney nickel under 50 ml of absolute ethanol, and then the reaction mixture was heated under reflux for 2 hours. The catalyst was removed by decantation and was washed with absolute ethanol. The combined ethanol solutions were evaporated in vacuo and the residue was dissolved in dichloromethane. The dichloromethane solution was dried ($Na_2SO_4$) and evaporated in vacuo to give 475 mg of 5-fluoro-2-oxindole, mp 121°–134° C.

In analogous fashion, 4-trifluoromethylaniline was reacted with t-butyl hypochlorite, ethyl 2-(methylthio)acetate and triethylamine followed by reduction of the 3-thiomethyl-5-trifluoromethyl-2-oxindole thus obtained with Raney nickel, to give 5-trifluoromethyl-2-oxindole, mp 189.5°–190.5° C.

PREPARATION 6

6-Fluoro-5-methyl-2-oxindole

An intimate mixture of 11.62 g (57.6 mmol) of N-(2-chloroacetyl)-3-fluoro-4-methylaniline and 30.6 g (229.5 mmol) of anhydrous aluminum chloride was heated to 210°–220° C. After 4 hours, the reaction mixture was cooled and then added to 100 ml of 1N hydrochloric acid and 50 ml of ice. A tan solid formed, which was collected by filtration and recrystallized from aqueous ethanol. Three crops were obtained, weighing 4.49 g, 2.28 g and 1.0 g, respectively. The first two crops comprised a mixture of isomers (4-fluoro-5-methyl and 6-fluoro-5-methyl-2-oxindoles). The crop weighing 1.0 g was further recrystallized from water to give 280 mg of the title compound, mp 168.5°–171° C.

PREPARATION 7

6-Phenyl-2-oxindole

To 3.46 g. (0.072 mole) of sodium hydride was added 50 ml. of dimethyl sulfoxide followed by the dropwise addition of a solution of 8.2 ml. (0.072 mole) of dimethyl malonate in 10 ml. of dimethyl sulfoxide, with stirring. After completion of the addition, stirring was continued for 1 hour, and then a solution of 10 g. (0.036 mole) of 4-bromo-3-nitrodiphenyl in 50 ml. of dimethyl sulfoxide was added. The reaction mixture was heated to 100° C. for 1 hour, cooled, and poured onto a mixture of ice-water containing 5 g. of ammonium chloride. The mixture thus obtained was extracted with ethyl acetate, and the extracts were washed with sodium chloride solution and dried using magnesium sulfate. Evaporation in vacuo to give an oil, which was chromatographed using silica gel and then recrystallized from methanol to afford 6 g. of dimethyl 2-(3-nitro-4-diphenylyl)malonate, m.p. 82°–83° C.

A portion (5 g.) of the above nitro compound was reduced with hydrogen over a platinum catalyst, in a mixture of 50 ml. of tetrahydrofuran and 10 ml. of methanol, at a pressure of ca 5 kg/cm$^2$, to give the corresponding amine. The latter compound was refluxed in ethanol for 16 hours, and then the product was recovered by solvent evaporation and recrystallized from methanol to give 1.1 g. of ethyl 6-phenyl-2-oxindole-1-carboxylate, m.p. 115°–117° C.

The above ethyl ester (1.0 g.) and 100 ml. of 6N hydrochloric acid was heated under reflux for 3 hours and then allowed to stand at room temperature for 3 days. The solid was collected by filtration and dried, to give 700 mg. of 6-phenyl-2-oxindole, m.p. 175°–176° C.

PREPARATION 8

5-Acetyl-2-oxindole

To 95 ml. of carbon disulfide was added 27 g. (0.202 mole) of aluminum chloride, followed by the dropwise addition of a solution of 3 ml. (0.042 mole) of acetyl chloride in 5 ml. of carbon disulfide, with stirring. Stirring was continued for 5 minutes and then 4.4 g. (0.033 mole) of 2-oxindole was added. The resulting mixture was heated under reflux for 4 hours and cooled. The carbon disulfide was removed by decantation and the residue was triturated under water and recovered by filtration. After drying, 3.2 g. of the title compound was obtained, m.p. 225°–227° C.

Reaction of 2-oxindole with benzoyl chloride and with 2-thenoyl chloride in the presence of aluminum chloride, substantially according to the above procedure, afforded the following compounds:
5-benzoyl-2-oxindole, m.p. 203°–205° C. (from CH3OH) and
5-(2-thenoyl)-2-oxindole, m.p. 211°–213° C. (from CH3CN).

PREPARATION 9

5-Bromo-2-oxindole can be prepared by bromination of 2-oxindole; see further Beckett et al., *Tetrahedron*, 24, 6093 (1968) and Sumpter et al., *Journal of the American Chemical Society*, 67, 1656 (1945).

5-n-Butyl-2-oxindole can be prepared by reaction of 5-n-butylisatin with hydrazine hydrate followed by sodium methoxide in ethanol, according to the procedure of Preparation 1. 5-n-Butylisatin can be prepared from 4-n-butylaniline by treatment with chloral hydrate and hydroxylamine, followed by cyclization with sulfuric acid, according to the procedure of Parts A and B of Preparation 3.

5-Ethoxy-2-oxindole can be prepared by conversion of 3-hydroxy-6-nitro-toluene into 3-ethoxy-6-nitrotoluene by standard methods (potassium carbonate and ethyl iodide in acetone), followed by conversion of the 3-ethoxy-6-nitrotoluene into 5-ethoxy-2-oxindole by the method described by Beckett et al., *Tetrahedron*, 24, 6093 (1968), for the conversion of 3-methoxy-6-nitrotoluene into 5-methoxy-2-oxindole. 5-n-Butoxy-2-oxindole can be prepared in like manner, but substituting n-butyl iodide for ethyl iodide.

5,6-Dimethoxy-2-oxindole can be prepared by the method of Walker, *Journal of the American Chemical Society*, 77, 3844 (1955).

7-Chloro-2-oxindole can be prepared by the method described in U.S. Pat. No. 3,882,236.

4-Thiomethyl-2-oxindole and 6-thiomethyl-2-oxindole can be prepared by the method described in U.S. Pat. No. 4,006,161. 5-n-Butylthio-2-oxindole can be prepared in like manner, but substituting 4-butylthioaniline for the 3-methylthioaniline.

5,6-Methylenedioxy-2-oxindole can be prepared by the method of McEvoy et al., *Journal of Organic Chemistry*, 38, 3350 (1973). 5,6-Ethylenedioxy-2-oxindole can be prepared in analogous fashion.

6-Fluoro-2-oxindole can be prepared according to Protiva et al., *Collection of Czechoslovakian Chemical Communications*, 44, 2108 (1979) and U.S. Pat. No. 4,160,032.

6-Trifluoromethyl-2-oxindole can be prepared according to Simet, *Journal of Organic Chemistry*, 28, 3580 (1963).

6-Methoxy-2-oxindole can be prepared according to Wieland et al., *Chemische Berichte*, 96, 253 (1963).

5-Nitro-2-oxindole can be prepared by the method of Sumpter et al., *Journal of the American Chemical Society*, 67, 499 (1945).

5-Cyclopropyl-2-oxindole and 5-cycloheptyl-2-oxindole can be prepared by reaction of 5-cyclopropylisatin and 5-cycloheptylisatin, respectively, with hydrazine hydrate followed by sodium methoxide in ethanol, according to the procedure of Preparation 1. 5-Cyclopropylisatin and 5-cycloheptylisatin can be prepared from 4-cyclopropylaniline and 4-cycloheptylaniline, respectively, by treatment with chloral hydrate and hydroxylamine, followed by cyclization with sulfuric acid, according to Parts A and B of Preparation 3.

PREPARATION 10

5-Amino-2-oxindole-1-carboxamide

To a solution of 5.0 g. of 5-nitro-2-oxindole-1-carboxamide in 110 ml. of N,N-dimethylformamide was added 0.5 g. of 10% palladium-on-carbon, and the resulting mixture was shaken under an atmosphere of hydrogen at an initial pressure of 5 kg/cm$^2$ until hydrogen uptake ceased. The catalyst was removed by filtration, and the filtrate was diluted with brine and extracted with ethyl acetate. The extracts were dried (MgSO4) and evaporated in vacuo to give a dark-colored oil which solidified after trituration under water. This afforded 3.0 g. of the title compound as a yellow solid, mp 189°–191° C.

PREPARATION 11

3-(2-Furoyl)-2-oxindole

To a stirred solution of 5.5 g (0.24 mole) of sodium in 150 ml of ethanol was added 13.3 g (0.10 mole) of 2-oxindole at room temperature. The resulting slurry was cooled to ice-bath temperature, and then 15.7 g (0.12 mole) of 2-furoyl chloride was added, dropwise, during 10–15 minutes. The ice-bath was removed, and an additional 100 ml of ethanol was added and then the reaction mixture was heated under reflux for 7 hours. The reaction mixture was allowed to stand overnight and then the solid was filtered off. The solid was added to 400 ml of water and the resulting mixture was acidified using concentrated hydrochloric acid. The mixture was cooled with ice and the solid was collected by filtration. The solid residue was recrystallized from 150 ml of acetic acid, affording 8.3 g of yellow crystals, mp 209°–210° (dec).

Analysis: Calcd. for C$_{13}$H$_9$O$_3$N: C, 68.72; H, 3.99; N, 6.17%. Found: C, 68.25; H, 4.05; N, 6.20%.

Reaction of 2-oxindole with the appropriate acid chloride using the above method, gave the following additional products:
3-(2-thenoyl)-2-oxindole, mp 189°–190° C., 17% yield;
3-(2-[2-thienyl]acetyl)-2-oxindole, mp 191°–192.5° C., 38% yield; and
3-(2-phenoxyacetyl)-2-oxindole, mp 135°–136° C., 42% yield.

PREPARATION 12

3-(3-Furoyl)-2-oxindole

To a stirred solution of 2.8 g (0.12 mole) of sodium in 200 ml of ethanol was added 13.3 g (0.10 mole) of 2-oxindole, followed by 16.8 g of ethyl 3-furoate. The mixture was heated under reflux for 47 hours, cooled and then the solvent was removed by evaporation in vacuo. The residue was triturated under 200 ml of ether, and the solid was collected by filtration and discarded. The filtrate was evaporated in vacuo, and the residue triturated under isopropyl alcohol and recovered by filtration. The solid was suspended in 250 ml of water, which was then acidified with concentrated hydrochloric acid. This mixture was stirred to give a solid, which was recovered by filtration. This latter solid was recrystallized from acetic acid followed by acetonitrile to give 705 mg of the title compound, mp 185°–186° C.

Analysis: Calcd. for $C_{13}H_9O_3N$: C, 68.72; H, 3.99; N, 6.17%. Found: C, 68.72; H, 4.14; N, 6.14%.

PREPARATION 13

5-Chloro-3-(2-thenoyl)-2-oxindole-1-carboxamide

A stirred slurry of 21.1 g (0.1 mole) of 5-chloro-2-oxindole-1-carboxamide and 26.9 g (0.22 mole) of 4-(N,N-dimethylamino)pyridine in 200 ml of N,N-dimethylformamide was cooled to ice-bath temperature, and then a solution of 16.1 g (0.11 mole) of 2-thenoyl chloride in 50 ml of N,N-dimethylformamide was added dropwise. Stirring was continued for ca. 30 minutes, and then the reaction mixture was poured into a mixture of 1 liter of water and 75 ml of 3N hydrochloric acid. The resulting mixture was cooled in an ice-bath, and then the solid was collected by filtration. The solid was recrystallized from 1800 ml of acetic acid to give 26.6 g of the title compound as fluffy, yellow crystals, m.p. 230° C. (dec.).

A sample of the title compound from a similar experiment gave the following results on elemental analysis.

Analysis: Calcd. for $C_{14}H_9ClN_2O_3S$: C, 52.42; H, 2.83; N, 8.74%. Found: C, 52.22; H, 2.81; N, 8.53%.

Preparation 14

Reaction of the appropriate 2-oxindole-1-carboxamide with the requisite acid chloride of the formula $R^1$—CO—Cl, substantially according to the procedure of Preparation 13, afforded the following compounds:

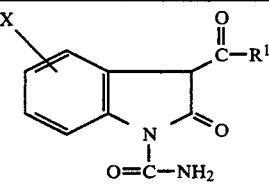

| X | $R^1$ | Melting Point (°C.)[1,2] | Calculated (%) C | H | N | Found (%) C | H | N |
|---|---|---|---|---|---|---|---|---|
| 5-Cl | 2-furyl | 234d | 55.18 | 2.98 | 9.20 | 55.06 | 3.09 | 9.32 |
| 5-Cl | 2-(2-thienyl)methyl | 240d[3] | 53.81 | 3.31 | 8.37 | 53.40 | 3.31 | 8.37 |
| 6-Cl | 2-furyl | 218–219 | 55.19 | 2.98 | 9.19 | 54.89 | 2.90 | 9.23 |
| 6-Cl | 2-thienyl | 201–202 | 52.44 | 2.83 | 8.74 | 51.86 | 3.03 | 8.61 |
| 6-Cl | 2-(2-thienyl)methyl | 219–220 | 53.83 | 3.31 | 8.37 | 53.70 | 3.45 | 8.38 |
| 5-F | 2-furyl | 232d | 58.34 | 3.15 | 9.72 | 57.99 | 3.13 | 9.70 |
| 5-F | 2-thienyl | 231d | 55.25 | 2.98 | 9.21 | 55.49 | 3.00 | 9.28 |
| 5-F | 2-(2-thienyl)methyl | 243d | 56.59 | 3.48 | 8.80 | 56.76 | 3.48 | 8.81 |
| 6-F | 2-furyl | 230.5–233.5 | 58.33 | 3.13 | 9.75 | 57.73 | 3.04 | 9.72 |
| 6-F | 2-thienyl | 117.5–120.5 | 55.26 | 2.96 | 9.21 | 55.14 | 2.91 | 9.15 |
| 6-F | 2-(2-thienyl)methyl | 214.5–217 | 56.61 | 3.48 | 8.80 | 55.97 | 3.52 | 8.65 |
| 5-$CF_3$ | 2-furyl | 235.5d | 53.26 | 2.68 | 8.28 | 52.84 | 2.96 | 8.17 |
| 5-$CF_3$ | 2-thienyl | 212.5d | 50.85 | 2.56 | 7.91 | 50.43 | 2.72 | 7.90 |
| 5-$CF_3$ | 2-(2-thienyl)methyl | 223.5d | 52.17 | 3.01 | 7.61 | 51.72 | 3.37 | 7.45 |
| 6-$CF_3$ | 2-furyl | 206–208 | 53.26 | 2.68 | 8.28 | 52.87 | 3.03 | 8.27 |
| 6-$CF_3$ | 2-thienyl | 177–180 | 50.86 | 2.56 | 7.91 | 50.69 | 2.75 | 7.96 |

[1] All compounds were recrystallized from acetic acid unless otherwise noted.
[2] The letter "d" in this column indicates that the compound melted with decomposition.
[3] Recrystallized from N,N—dimethylformamide.

PREPARATION 15

5-Chloro-3-acetyl-2-oxindole-1-carboxamide

A stirred slurry of 842 mg (4.0 mmole) of 5-chloro-2-oxindole-1-carboxamide and 1.08 g (8.8 mmole) of 4-(N,N-dimethylamino)pyridine in 15 ml of N,N-dimethylformamide was cooled to ice-bath temperature, and then a solution of 449 mg (4.4 mmole) of acetic anhydride in 5 ml of N,N-dimethylformamide was added dropwise. Stirring was continued for ca. 30 minutes, and then the reaction mixture was poured into a mixture of 75 ml of water and 3 ml of 3N hydrochloric acid. The resulting mixture was cooled in an ice-bath and the solid was recovered by filtration. The solid was recrystallized from acetic acid to give 600 mg of fluffy, pale pink crystals, m.p. 237.5° C. (dec.).

Analysis: Calcd. for $C_{11}H_9ClN_2O_3$: C, 52.29; H, 3.59; N, 11.09%. Found: C, 52.08; H, 3.63; N, 11.04%.

I claim:
1. A compound of the formula

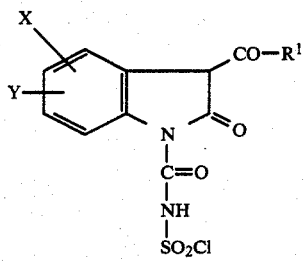

wherein
X and Y are each selected from the group consisting of hydrogen, fluoro, chloro, bromo, alkyl having 1 to 4 carbons, alkoxy having 1 to 4 carbons, alkylthio having 1 to 4 carbons, nitro and trifluoromethyl; or X and Y when taken together are a 4,5-, 5,6- or 6,7-methylenedioxy group; and
R¹ is selected from the group consisting of alkyl having 1 to 6 carbons, cycloalkyl having 3 to 7 carbons, phenyl, substituted phenyl, phenylakyl having 1 to 3 carbons in said alkyl, phenoxyalkyl having 1 to 3 carbons in said alkyl, (substituted phenoxy)alkyl having 1 to 3 carbons in said alkyl, furyl, thienyl, alkylfuryl having 1 to 3 carbons in said alkyl, alkylthienyl having 1 to 3 carbons in said alkyl, furylalkyl having 1 to 3 carbons in said alkyl, theinylakyl having 1 to 3 carbons in said alkyl and bicyclolo heptan-2-yl;
wherein the substituent on said substituted phenyl group and said substituted phenoxy group is selected from the group consisting of fluoro, chloro, bromo, alkyl having 1 to 4 carbons and alkoxy having 1 to 4 carbons.

2. A compound according to claim 1, wherein one of X and Y is hydrogen, and the other is 5- or 6- chloro, fluoro or trifluoromethyl.

3. The compound according to claim 2, wherein X is hydrogen, Y is 5-chloro and R¹ is 2-thienyl.

4. A compound according to claim 1, wherein X is 5-chloro or 5-fluoro and Y is 6-chloro or 6-fluoro.

* * * * *